US00PP21839P2

(12) United States Plant Patent
Kapusta

(10) Patent No.: US PP21,839 P2
(45) Date of Patent: Apr. 5, 2011

(54) ***LONICERA* PLANT NAMED 'INOV86'**

(50) Latin Name: *Lonicera periclymenum*
Varietal Denomination: Inov86

(75) Inventor: Véronique Kapusta, Beaucouzé (FR)

(73) Assignees: Institut National de la Recherche Agronomique, Paris (FR), part interest; Saphinov S.N.C., Beaufort (FR), part interest ( * ) Notice: Subject to any disclaimer, the term of this patent is extended or adjusted under 35 U.S.C. 154(b) by 0 days.

(21) Appl. No.: 12/584,231

(22) Filed: Sep. 2, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner* — June Hwu
(74) *Attorney, Agent, or Firm* — Penny J. Aguirre

(57) ABSTRACT

A new cultivar of *Lonicera,* 'Inov86', characterized by its dense flowering display of large fragrant inflorescences of large flowers in June and July that emerge with dark purple red buds and turn dark pink and white when fully open and turn a creamy yellow-orange as they mature, its resistance to powdery mildew, black spot, and green fly and its vigorous growth habit.

2 Drawing Sheets

Botanical classification: *Lonicera pericylmenum.*
Variety denomination: 'Inov86'.

RELATED APPLICATIONS

This application is co-pending with a U.S. Plant patent application for a cultivar discovered from similar parentage entitled *Lonicera* Plant Named 'Inov71' (U.S. patent application Ser. No. 12/584,237).

BACKGROUND OF THE INVENTION

The present invention relates to a new and distinct cultivar of *Lonicera,* botanically of hybrid origin, and will be referred to hereafter by its cultivar name, 'Inov86'. 'Inov86' is a new cultivar of honeysuckle, a vine grown for use as an ornamental landscape plant.

The new Invention arose from an ongoing controlled breeding program by the Inventor in Beaucouzé, France. 'Inov86' originated as a seedling of a mutant of *Lonicera periclymenum* 'Florida' (not patented, syns. *Lonicera periclymenum* 'Serotina Florida' or *Lonicera periclymenum* var. *serotina* 'Florida') that had been obtained by gamma ray irradiation at a level of 30Gy in the Inventor's laboratory in summer of 1996. The male parent is unknown but 'Inov86' is thought to result from self-pollination. The new cultivar was selected as a single unique plant in 2001.

Asexual reproduction of the new cultivar was first accomplished by the Inventor using softwood stem cuttings in 2002 in Beaucouzé, France. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial plot for five years in Beaucouzé, France. These attributes in combination distinguish 'Inov86' as a unique cultivar of *Lonicera.*

1. 'Inov86' exhibits larger inflorescences and large flowers.

2. 'Inov86' exhibits resistance to powdery mildew, black spot, and green fly.
3. 'Inov86' blooms in June and July with fragrant flowers that emerge with dark purple red buds and turn dark pink and white when fully open and turn a creamy yellow-orange as they mature.
4. 'Inov86' exhibits a vigorous growth habit.

In comparison to the female parent plant (and probable male parent), 'Florida', 'Inov86' differs in having a larger flowers and larger inflorescences, in having better resistance to powdery mildew, black spot, and green fly, and in having a more vigorous growth habit. 'Inov86' is more resistant to disease and green fly than its sister seedling, 'Inov71' and 'Inov86' has flowers that are larger and more red in color, larger inflorescences and a more vigorous growth habit than 'Inov71'. 'Inov86' can also be compared to the cultivars 'Scentsation' (U.S. Plant Pat. No. 16,240) and 'Graham Thomas' (not patented), which are similar in having abundant, fragrant flowers, however 'Inov86' can also be distinguished from these cultivars in having larger flowers and larger inflorescences.

BRIEF DESCRIPTION OF THE DRAWING

The accompanying colored photographs were taken in mid summer and illustrate the overall appearance and distinct characteristics of 5 year-old plants the new *Lonicera* as grown in a trial garden in Beaucouzé, France.

The photograph in FIG. 1 provides an overall view of 'Inov86' in bloom.

Figure 1:
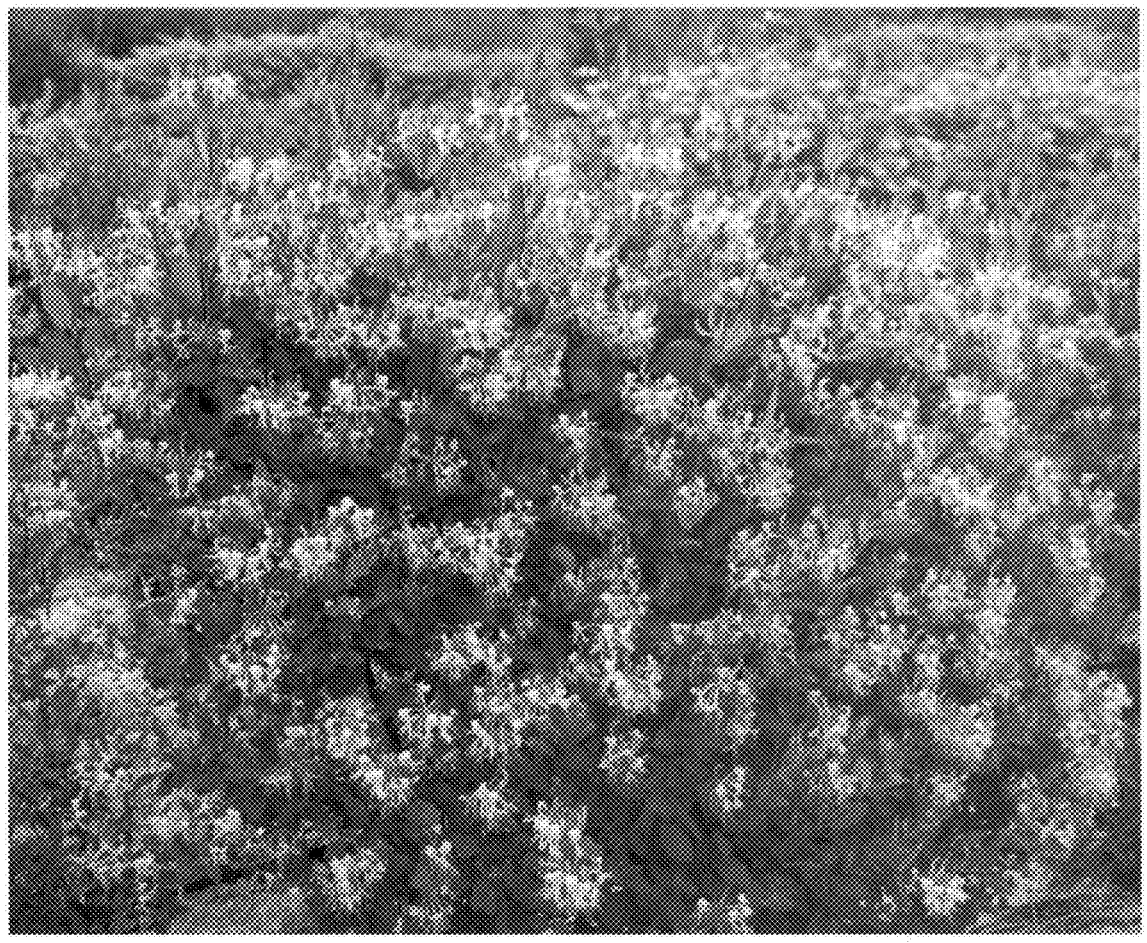
Figure 2:
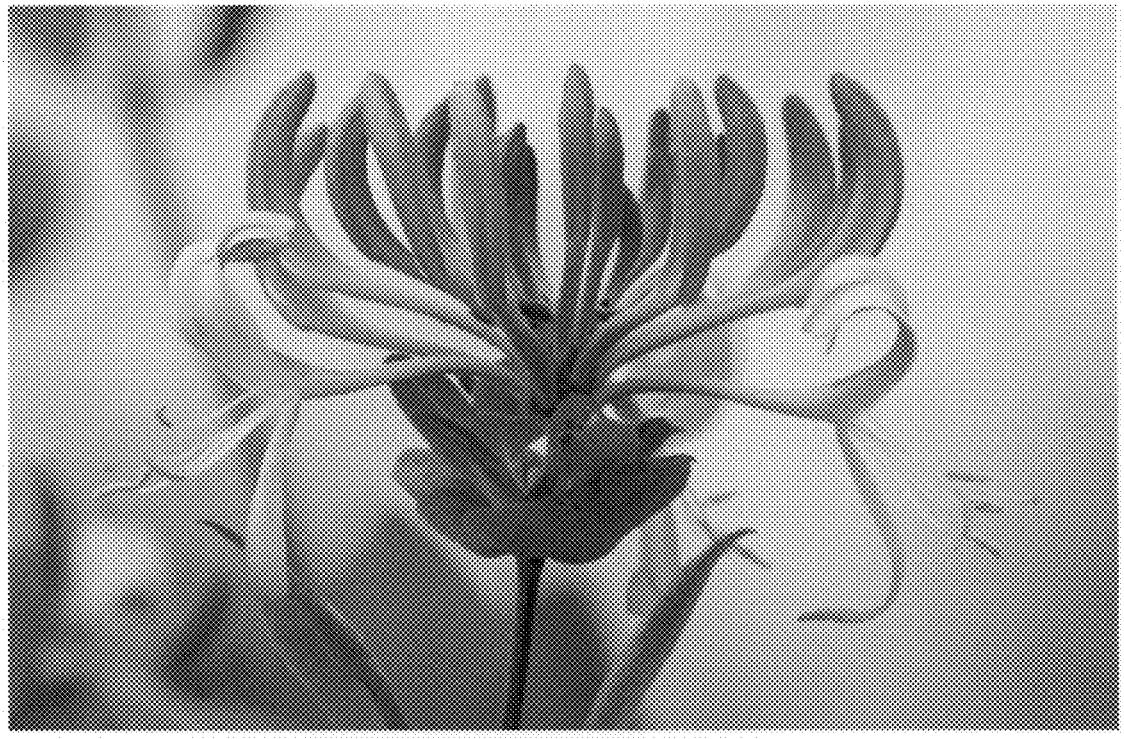
Figure 3:
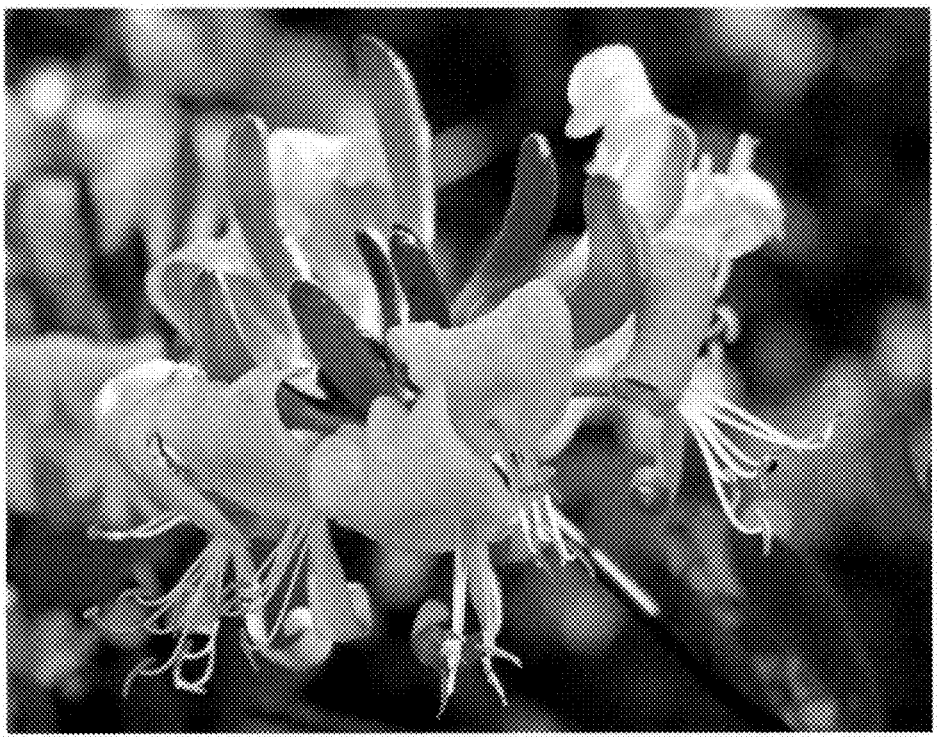

The photograph in FIG. 2 provides a close-up view of an inflorescence of 'Inov86' when the flowers are just opening and FIG. 3 provides a close-up view of a mature inflorescence of 'Inov86'. The colors in the photographs may differ slightly from the color values cited in the detailed botanical description, which accurately describe the colors of the new *Lonicera.*

DETAILED BOTANICAL DESCRIPTION

The following is a detailed description of 5 year-old plants the new *Lonicera* as grown in a trial garden in Beaucouzé, France. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Botanical classification.*—*Lonicera periclymenum* 'Inov86'.

*Parentage.*—Seedling of a mutant obtained by Gamma irradiation of *Lonicera periclymenum.*

*Blooming period.*—Blooms in June and July in Beaucouzé, France.

*Plant habit.*—Perennial climbing vine.

*Length.*—Reaches 2 to 3 m in length and about 2 m in width.

*Diseases and pests.*—Has shown good resistance to powdery mildew, black spot, and green fly.

*Hardiness.*—U.S.D.A. Zones 4 to 8.

*Root description.*—Fibrous.

Growth and propagation:

*Propagation.*—Terminal, softwood stem cuttings.

*Growth rate.*—Vigorous.

Stem description:

*Shape.*—Round.

*Stem color.*—New growth; 187A and 187B, mature wood and bark about 177A.

*Stem size.*—Old wood; ranges about 2.5 cm in diameter near base to 4 mm in diameter on lateral branches, new growth; average of 2 mm in diameter, up to 3 m in length.

*Stem surface.*—New growth; Glabrous, mature wood is dull and smooth and becoming bark-like as it ages.

*Internode length.*—An average of 2 cm.

*Branching.*—Well branched with new growth emerging in opposite arrangement from axillary nodes.

Foliage description:

*Leaf shape.*—Elliptic.

*Leaf division.*—Simple.

*Leaf base.*—Cuneate.

*Leaf apex.*—Acute to cuspidate.

*Leaf fragrance.*—None.

*Leaf venation.*—Pinnate, only mid rib is conspicuous, color on upper surface, 146C, color on lower surface; 143D.

*Leaf margins.*—Entire.

*Leaf arrangement.*—Opposite.

*Leaf attachment.*—Petiolate.

*Leaf surface.*—Glabrous on upper surface and lower surface.

*Leaf internode length.*—An average of 2 cm.

*Leaf size.*—Average of 4.5 cm in length and 2.5 cm in width.

*Leaf color.*—Newly expanded leaves upper surface; ranges from 144A to 144B, newly expanded leaves lower surface; 143C, mature leaves upper surface; ranges from 137A to 137B, mature leaves lower surface; ranges from 138B to 138C.

*Petioles.*—Average of 5 mm in length and 1.8 mm in width, 143D in color, glabrous surface.

*Stipules.*—None.

Inflorescence description:

*Inflorescence type.*—Comprised whorls (contracted corymb) of tubular flowers at terminus of lateral branches with sometime with smaller inflorescences on upper auxiliary nodes.

*Inflorescence size.*—Ranges from 5 to 6 cm in height and 9 to 10 cm in width.

*Flower buds.*—Oblanceolate in shape, ranges from 5 to 5.2 cm in length, an average of 6 mm in width, color; inner buds are 59A and outer buds are 64A and 64B in color.

*Flower fragrance.*—Fragrant.

*Lastingness of inflorescence.*—Inflorescence blooms for 2 to 3 weeks with individual flowers lasting about 4 days, lower whorls begin opening first, self-cleaning.

*Flower quantity.*—21 to 24 flowers per inflorescence.

*Flower type.*—Tubular, 2-lipped.

*Flower aspect.*—Upright to outward.

*Flower size.*—Average of 1.4 cm in diameter and 7 cm in depth (including exserted stamens and pistil).

*Peduncles.*—None, sessile to stem.

*Bracts.*—None observed.

*Pedicels.*—None, sessile to stem.

*Calyx.*—5-starred, inconspicuous, about 2 mm in diameter and depth.

*Sepals.*—5, un-fused portion in triangular acute tip, fused base, 147B in color, entire margin on tips, glabrous surface.

*Petals.*—5, fused to tube at base, tube ranges from 3.3 to 3.5 cm in length and an average of 5 mm in width, free portion is 2-lipped with upper lip comprised of 4 fused petals flared outward to reflexed and lower lip comprised of 1 petal that is reflexed, fused petals are about 5.5 cm in length and 1.6 cm in width combined, free portion of upper lip petals are triangular in shape and about 4.5 mm in length and width, free portion of lower lip petal is oblong in shape and about 5 cm in length and 5 mm in width, all free petals portions have a rounded apex and entire margin, outer and inner surface is glabrous, color of inner surface of tube and free portions; 155D when opening and 159D when fully open, color of outer surface of tube and free portions; 72B and 72C when opening and 70C and 72C when fully open, color of both surfaces when fading; 18C and 18D.

Reproductive organs:

*Gynoecium.*—1 pistil, an average of 5.8 cm in length and exserted beyond corolla, style is about 5.6 cm in length, and 155A in color, stigma is about 2 mm in diameter and 0.7 mm in depth, flattened globose in shape and 145C in color, ovary is inferior, ovoid in shape and ranges from 145A and 144C in color.

*Androcoecium.*—5 stamens, about 5.4 cm in length and exserted beyond corolla, filaments are 155A in color, about 5.3 cm in length, anthers are about 4 mm in length, dorsifixed, 24B in color when flower is fully open, pollen is abundant in quantity and 24B in color.

*Fruit and seed.*—True berry, round in shape, about 1 cm in diameter, 44A in color.

It is claimed:

1. A new and distinct cultivar of *Lonicera* plant named 'Inov86' as herein illustrated and described.

* * * * *